(12) United States Patent
Mann et al.

(10) Patent No.: US 10,342,233 B2
(45) Date of Patent: Jul. 9, 2019

(54) CONTROL OF AQUATIC WEEDS USING COMBINATIONS OF 4-AMINO-3-CHLORO-6-(4-CHLORO-2-FLUORO-3-METHOXYPHENYL)PYRIDINE-2-CARBOXYLIC ACIDS AND OTHER AQUATIC HERBICIDES

(71) Applicant: Dow AgroSciences LLC, Indianapolis, IN (US)

(72) Inventors: Richard K. Mann, Indianapolis, IN (US); Carla N. Yerkes, Crawfordsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/745,515

(22) PCT Filed: Jul. 11, 2016

(86) PCT No.: PCT/US2016/041735
§ 371 (c)(1),
(2) Date: Jan. 17, 2018

(87) PCT Pub. No.: WO2017/014973
PCT Pub. Date: Jan. 26, 2017

(65) Prior Publication Data
US 2018/0206492 A1 Jul. 26, 2018

Related U.S. Application Data

(60) Provisional application No. 62/193,779, filed on Jul. 17, 2015.

(51) Int. Cl.
*A01N 43/40* (2006.01)
*A01N 43/90* (2006.01)
*A01N 59/20* (2006.01)
*C07D 213/79* (2006.01)
*A01N 43/08* (2006.01)

(52) U.S. Cl.
CPC ............. *A01N 43/40* (2013.01); *A01N 43/08* (2013.01); *A01N 43/90* (2013.01); *A01N 59/20* (2013.01); *C07D 213/79* (2013.01); *A01N 2300/00* (2013.01)

(58) Field of Classification Search
None
See application file for complete search history.

(56) References Cited

U.S. PATENT DOCUMENTS

| | | | |
|---|---|---|---|
| 4,012,221 A | 3/1977 | Walker et al. | |
| 2009/0298691 A1 | 12/2009 | Koschnick et al. | |
| 2013/0310256 A1 | 11/2013 | Yerkes et al. | |
| 2015/0018213 A1 | 1/2015 | Koshnick et al. | |

FOREIGN PATENT DOCUMENTS

| | | |
|---|---|---|
| CN | 105580821 A | 5/2016 |
| WO | 2009111262 A1 | 9/2009 |
| WO | 2015/089247 A1 | 6/2015 |
| WO | 2015/116745 A1 | 8/2015 |
| WO | 2017/044585 A1 | 3/2017 |

*Primary Examiner* — Alton N Pryor

(57) ABSTRACT

Methods for controlling aquatic weeds using halauxifen or florpyrauxifen or agriculturally acceptable esters or salts thereof in combination with one or more of diquat dibromide, copper salts, endothal, or fluridone, or agriculturally acceptable salts or esters thereof, are described. The herbicidal compositions described allow for effective control and/or selectivity when treating a body of water, to control target aquatic weed populations, such as alligatorweed, yellow nutsedge, barnyardgrass, early watergrass, *Echinochloa* species, saramollagrass, Chinese sprangletop, hydrilla, Eurasian watermilfoil and/or curlyleaf pondweed.

28 Claims, No Drawings

CONTROL OF AQUATIC WEEDS USING COMBINATIONS OF 4-AMINO-3-CHLORO-6-(4-CHLORO-2-FLUORO-3-METHOXYPHENYL)PYRIDINE-2-CARBOXYLIC ACIDS AND OTHER AQUATIC HERBICIDES

BACKGROUND

Aquatic plants commonly arise as undesired weeds in waters and wetlands. Three such weeds are *hydrilla*, curlyleaf pondweed, and watermilfoil, including Eurasian watermilfoil. The treatment of bodies of water to eliminate or control the undesired aquatic weeds is often complicated by the fact that the agent used to control the undesired weed may also adversely affect the health of desirable or native plant life. Aquatic herbicides need to be in contact with aquatic (submersed, immersed or floating) plants for a period of time to be effective. Some herbicides require long exposures (one or more months) to control certain submersed, immersed, or floating plants in water, which can adversely affect non-target plant species. Long exposure times can be difficult to achieve in a fluid environment. Insufficient exposure can lead to poor efficacy or failed treatments. Thus, methods or techniques to reduce exposure times and/or reduce the concentrations of agents used to control aquatic weeds may benefit efficacy and/or selectivity.

The efficacy of herbicidal agents against the target aquatic weeds depends on multiple factors, including but not limited to the application dose, the active ingredient, the specific formulation, the plant type, plant susceptibility, climatic conditions, water and sediment conditions, and herbicide exposure time. At times, an inability to control an undesired aquatic weed can be overcome simply by increasing the application rate or concentration of a particular herbicidal agent. However, this is not always the case, and higher application rates can cause adverse or undesired effects on beneficial aquatic plants and aquatic organisms and may not adequately compensate for rates necessary to control the targeted aquatic plant.

SUMMARY

Described herein are herbicidal compositions useful for controlling aquatic weeds in a body of water. The herbicidal compositions comprise a herbicidally effective amount of (a) a compound of formula (I) or a compound of formula (II),

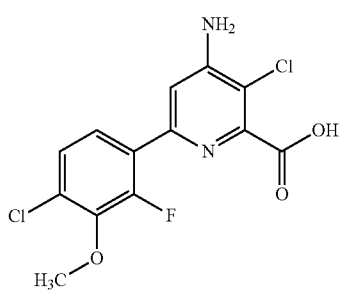

(I)

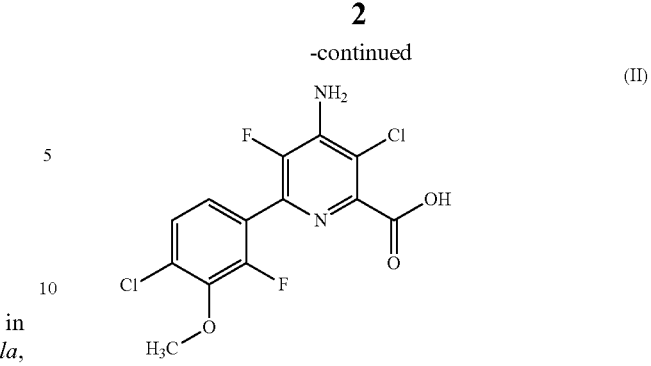

(II)

or an agriculturally acceptable salt or ester thereof, and (b) one or more of copper salts, diquat dibromide, endothal, or fluridone, or agriculturally acceptable salts or esters thereof.

Also described herein are methods for controlling aquatic weeds in a body of water using the herbicidal compositions described herein. The methods include providing in the body of water a composition containing a herbicidally effective amount of a composition as described herein.

DETAILED DESCRIPTION

I. Definitions

The following terms have the indicated meanings when used herein:

Compounds of formulas (I) and (II) and agriculturally acceptable salts and esters thereof are described in U.S. Pat. No. 7,314,849 (B2), which is incorporated herein by reference in its entirety.

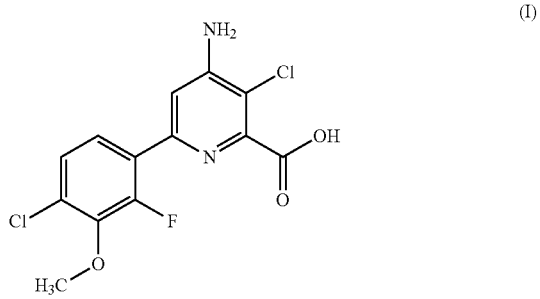

(I)

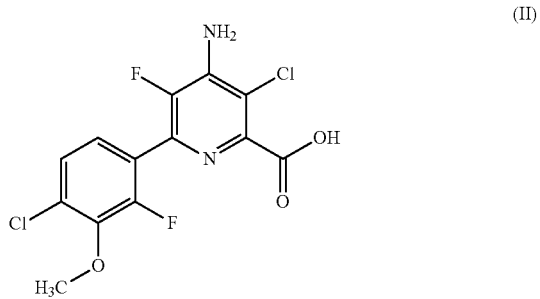

(II)

Compound I refers to the compound of formula (I), i.e. 4-amino-3-chloro-6-(4-chloro-2-fluoro-3-methoxyphenyl) pyridine-2-carboxylic acid, known as halauxifen, and to agriculturally acceptable salts and esters thereof. A preferred ester of Compound (I) is the methyl ester. Compound II refers to the compound of formula (II), i.e. 4-amino-3-chloro-5-fluoro-6-(4-chloro-2-fluoro-3-methoxyphenyl) pyridine-2-carboxylic acid, known as florpyrauxifen, and to agriculturally acceptable salts and esters thereof. A preferred ester of Compound (II) is the benzyl ester.

Compounds I and II are described in U.S. Pat. No. 7,314,849 (B2) as belonging to a family of compounds with a broad spectrum of weed control activity against woody plants, broadleaf and grass weeds, and sedges in crops such as corn, rice and cereals. US2009/0062121A1 indicates that Compound I is a preferred compound for the control of weeds in cereal crops including spring, winter and durum wheat, spring and winter barley, oats, and triticale. U.S. Pat. No. 8,598,084 (B2) provides that Compound I is used for the control of weeds in cereal crops, including spring, winter, and durum wheat, and spring and winter barley, and that the methyl ester of the compound of formula (I) controls broadleaf weeds such as *Papaver, Galium, Lamium, Kochia, Amaranthus, Aeschynomene, Sesbania,* and *Monochoria,* and sedge species such as *Cyperus* and *Schoenoplectus.* U.S. Pat. No. 8,883,688 (B2) shows that Compound II is used for the control of weeds in cereal crops, including rice and wheat, and that the benzyl ester of the compound of formula (II) controls grass weed species such as *Echinochloa* and *Brachiaria*, also known as *Urochloa*, broadleaf weed species such as *Amaranthus, Conyza, Aeschynomene, Sesbania, Murdannia, Heteranthera* and *Sagittaria*, and sedge species such as *Cyperus* and *Schoenoplectus*.

As used herein, copper sulfate is copper(II) sulfate or cupric sulfate, which has the following structure:

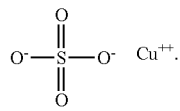

Exemplary herbicidal uses are provided in Shaner, D. L., Ed. *Herbicide Handbook.* Lawrence: Weed Science Society of America, 2014 (hereafter "*Herbicide Handbook*, Tenth Edition, 2014"). Exemplary uses of copper sulfate include, but are not limited to, control of algal growth in impounded waters, lakes, ponds, reservoirs, and irrigation conveyance systems.

As used herein, mixed copper ethanolamine complex or copper chelate, includes the following:

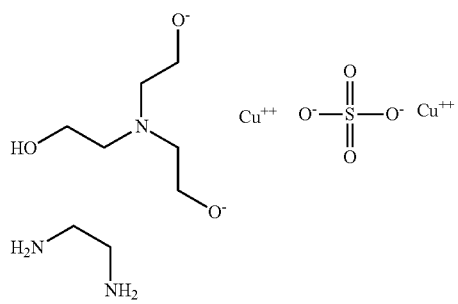

Exemplary herbicidal uses are provided in Shaner, D. L., Ed. *Herbicide Handbook*, Tenth Edition, 2014. Exemplary uses of copper chelate include, but are not limited to, control of algal growth in impounded waters, lakes, ponds, reservoirs, stock tanks and irrigation conveyance systems.

As used herein, diquat is 9,10-dihydro-8a,10a-diazoniaphenanthrene, 6,7-dihydrodipyrido[1,2-a:2',1'-c]pyrazine-5,8-diium, or 1,1'-ethylene-2,2'-bipyridyldiylium, which has the following structure:

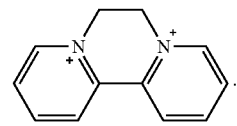

Exemplary herbicidal uses are provided in Shaner, D. L., Ed. *Herbicide Handbook*, Tenth Edition, 2014. Exemplary chemical forms of diquat include, but are not limited to, diquat dibromide. Exemplary uses of diquat include, but are not limited to, post-emergence control of cattails, algal control of submerged aquatic weeds such as bladderwort, coontail, and *Elodea* and floating aquatic weeds such as pennywort, *salvinia*, and water hyacinth in ponds, lakes, and drainage ditches.

As used herein, endothal or endothall is 7-oxabicyclo[2.2.1]heptane-2,3-dicarboxylic acid, which has the following structure:

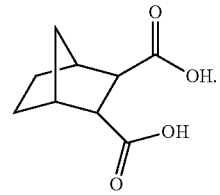 [SMILES: O=C(O)C1C2CCC(C2)C1C(=O)O]

Exemplary chemical forms of endothal include, but are not limited to, salts of endothal, such as endothal-diammonium, endothal-dipotassium, and endothal-disodium. Exemplary herbicidal uses are provided in Shaner, D. L., Ed. *Herbicide Handbook*, Tenth Edition, 2014. Exemplary uses of enthodal include, but are not limited to, control of algal growth and several other aquatic weeds such as pondweed, bureed, milfoil, and coontail by spray application or water injection into ponds, lakes, and canals.

As used herein, fluridone is 1-methyl-3-phenyl-5-($\alpha,\alpha,\alpha$-trifluoro-m-tolyl)-4-pyridone, which has the following structure:

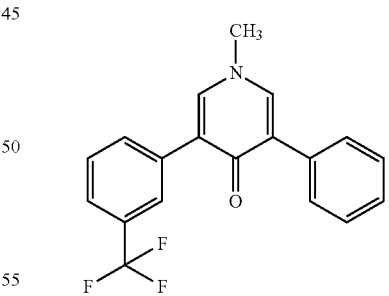

Exemplary herbicidal uses are provided in Shaner, D. L., Ed. *Herbicide Handbook*, Tenth Edition, 2014. Exemplary uses of fluridone include its use as an aquatic herbicide in ponds, in lakes and reservoirs and on treated surfaces of drainage canals, irrigation canals, and rivers. It can be applied to the water surface or subsurface or as a bottom application just above the hydrosoil. Fluridone controls most submerged and emerged aquatic plants, including but not limited to, bladderwort, coontail, *elodea*, watermilfoil, naiad, pondweeds, *hydrilla* and paragrass.

The term herbicide is used herein to mean an active ingredient that kills, controls or otherwise adversely modifies the growth of plants. As used herein, a herbicidally effective or vegetation controlling amount is an amount of active ingredient that causes a "herbicidal effect", i.e. an adversely modifying effect and includes deviations from natural development, killing, regulation, desiccation, growth inhibition, growth reduction and retardation.

As used herein, selective control of undesirable vegetation means preventing, reducing, killing, or otherwise adversely modifying the development of the undesirable vegetation at any stage of growth in a body of water.

As used herein, the terms "plants" and "vegetation" include, but are not limited to, germinant seeds, emerging seedlings, plants emerging from vegetative propagules and established vegetation.

As used herein, immature vegetation refers to small vegetative plants prior to reproductive stage, and mature vegetation refers to vegetative plants during and after the reproductive stage.

As used herein, a body of water includes, but is not limited to, ponds, lakes, rivers, streams, canals and reservoirs, treated surfaces of drainage canals, irrigation canals, and water containment structures.

As used herein, applying a herbicide or herbicidal composition means delivering it directly to the targeted vegetation or to the area adjacent to the targeted vegetation (i.e., the locus thereof) or to the area where control of undesired vegetation is desired, such as above the water surface, at the water surface, subsurface, or at the bottom just above the hydrosoil, or is water injected.

As used herein, agriculturally acceptable salts and esters of the compound of formula (I), of the compound of formula (II), e.g., copper salts, diquat dibromide, endothal, or fluridone, refer to salts and esters that (a) do not substantially affect the herbicidal activity and (b) are or can by hydrolyzed, oxidized, metabolized, or otherwise converted in plants or in the environment (e.g., water, air, or soil) to the corresponding carboxylic acid which, depending on the pH, may be in the dissociated or undissociated form. Exemplary salts include those derived from alkali or alkaline earth metals and those derived from ammonia and amines. Exemplary cations include sodium, potassium, magnesium, and ammonium cations of the formula:

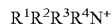

wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

II. Compositions

A. Synergistic Combinations

Herbicidal compositions containing synergistically effective amounts of (a) a compound of formula (I) or a compound of formula (II), or an agriculturally acceptable salt or ester thereof, and (b) one or more of diquat dibromide, copper salts, endothal, or fluridone, or agriculturally acceptable salts or esters thereof are described herein. In some embodiments, the copper salts are copper sulfate and mixed copper ethanolamine complex or copper chelate. The compositions described herein are unexpectedly effective when applied to aquatic plants at very low concentrations, and/or can be used to improve selectivity for non-target aquatic weeds, thus having less adverse effect on non-target plant species due to reduced concentration of, and/or exposure to, the herbicidal agents.

The concentration of the active ingredients in the compositions described herein can be from 0.0005 to 98 percent by weight or from 0.0006 to 90 percent by weight. In compositions designed to be employed as concentrates, the active ingredients can be present in a concentration from 0.1 to 98 weight percent or from 0.5 to 90 weight percent. Such compositions can be diluted with an inert carrier, such as water, before application. The diluted compositions usually applied to weeds or the locus of weeds can contain 0.0000006 to 10.0 weight percent active ingredient or contain 0.000001 to 5.0 weight percent.

In the compositions and methods of use thereof described herein, a compound of formula (I) or a compound of formula (II), or an agriculturally acceptable salt or ester thereof, can be used in combination with copper sulfate. With regard to these compositions, the weight ratio of a compound of formula (I) or a compound of formula (II), or an agriculturally acceptable salt or ester thereof, to copper sulfate can be within the range from about 1:8000 to about 2:1, from about 1:7000 to about 1.9:1, from about 1:6000 to about 1.8:1, from about 1:5000 to about 1.7:1, from about 1:4000 to about 1.6:1, from about 1:3000 to about 1.5:1, from about 1:2000 to about 1.4:1, from about 1:1000 to about 0.25:1, from about 1:750 to about 1.2:1, from about 1:500 to about 1.1:1, from about 1:250 to about 1:1, from about 1:100 to about 1:1.1, from about 1:90 to about 0.85:1, from about 1:80 to about 0.75:1, from about 1:70 to about 0.5:1, from about 1:60 to about 0.25:1, from about 1:55 to about 1:6. The weight ratio of a compound of formula (I) or a compound of formula (II), or an agriculturally acceptable salt or ester thereof to copper sulfate can be within the range from about 1:27 to about 1:4.5. Additionally, the weight ratio of a compound of formula (I) or a compound of formula (II), or an agriculturally acceptable salt or ester thereof to copper sulfate can be within the range from about 1:14 to about 1:9.

In the compositions and methods of use thereof described herein, a compound of formula (I) or a compound of formula (II), or an agriculturally acceptable salt or ester thereof, can be used in combination with copper chelate. With regard to the compositions, the weight ratio of a compound of formula (I) or a compound of formula (II), or an agriculturally acceptable salt or ester thereof, to copper chelate can be within the range from about 1:40000 to about 2.5:1, from about 1:20000 to about 2:1, from about 1:10000 to about 1.5:1, from about 1:5000 to about 1:1, from about 1:2500 to about 1:2, from about 1:1000 to about 1:3, from about 1:800 to about 1:20, from about 1:700 to about 1:10, from about 1:600 to about 1:4.8, from about 1:400 to about 1:8, from about 1:240 to about 1:36. The weight ratio of a compound of formula (I) or a compound of formula (II), or an agriculturally acceptable salt or ester thereof to copper chelate can be within the range from about 1:250 to about 1:15. Additionally, the weight ratio of a compound of formula (I) or a compound of formula (II), or an agriculturally acceptable salt or ester thereof to copper chelate can be within the range from about 1:80 to about 1:50.

In the compositions and methods of use thereof described herein, a compound of formula (I) or a compound of formula (II), or an agriculturally acceptable salt or ester thereof, can be used in combination with diquat dibromide. With regard to these compositions, the weight ratio of a compound of formula (I) or a compound of formula (II), or an agriculturally acceptable salt or ester thereof, to diquat dibromide can be within the range from about 1:112000 to about 1:6, from about 1:112000 to about 1:14, from about 1:84000 to about 1:21, from about 1:56000 to about 1:28, from about 1:28000 to about 1:56, from about 1:14000 to about 1:60, from about 1:7000 to about 1:15, from about 1:1134 to about 1:16, from about 1:900 to about 1:32, from about 1:800 to about 1:68, from about 1:400 to about 1:40, from about 1:300 to about 1:48. The weight ratio of a compound of formula (I) or a compound of formula (II), or an agriculturally acceptable salt or ester thereof to diquat dibromide can be within the range from about 1:220 to about 1:6. Additionally, the weight ratio of a compound of formula (I) or a compound of formula (II), or an agriculturally acceptable salt or ester thereof to diquat dibromide can be within the range from about 1:54 to about 1:27.

In the compositions and methods of use thereof described herein, a compound of formula (I) or a compound of formula (II), or an agriculturally acceptable salt or ester thereof, can be used in combination with endothal or an agriculturally acceptable salt or ester thereof. With regard to these compositions, the weight ratio of a compound of formula (I) or a compound of formula (II), or an agriculturally acceptable salt or ester thereof, to endothal or an agriculturally acceptable salt or ester thereof can be within the range from about 1:40000 to about 10:1, from about 1:20000 to about 5:1, from about 1:10000 to about 2.5:1, from about 1:5000 to about 1.25:1, from about 1:2500 to about 1:1, from about 1:1900 to about 1:2, from about 1:1500 to about 1:4, from about 1:1000 to about 1:6, from about 1:500 to about 1:16, from about 1:200 to about 1:20, from about 1:150 to about 1:25, from about 1:125 to about 1:30, from about 1:100 to about 1:38. The weight ratio of a compound of formula (I) or a compound of formula (II), or an agriculturally acceptable salt or ester thereof to endothal or an agriculturally acceptable salt or ester thereof can be within the range from about 1:269 to about 1:8. Additionally, the weight ratio of a compound of formula (I) or a compound of formula (II), or an agriculturally acceptable salt or ester thereof to endothal or an agriculturally acceptable salt or ester thereof can be within the range from about 1:68 to about 1:33.

In the compositions and methods of use thereof described herein, a compound of formula (I) or a compound of formula (II), or an agriculturally acceptable salt or ester thereof, can be used in combination with fluridone. With regard to these compositions, the weight ratio of a compound of formula (I) or a compound of formula (II), or an agriculturally acceptable salt or ester thereof, to fluridone can be within the range from about 1:1200 to about 100:1, from about 1:1000 to about 90:1, from about 1:800 to about 80:1, from about 600 to about 70:1, from about 1:400 to about 60:1, from about 1:200 to about 50:1, from about 1:100 to about 40:1, from about 1:48 to about 33.3:1, from about 1:40 to about 15:1, from about 1:30 to about 7.5:1, from about 1:25 to about 3:1, from about 1:20 to about 1.67:1, from about 1:10 to about 1.5:1, from about 1:6 to about 1.25:1, from about 1:240 to about 1:7.5. The weight ratio of a compound of formula (I) or a compound of formula (II), or an agriculturally acceptable salt or ester thereof to fluridone can be within the range from about 1:6 to about 14:1. Additionally, the weight ratio of a compound of formula (I) or a compound of formula (II), or an agriculturally acceptable salt or ester thereof to fluridone can be within the range from about 1:1.35 to about 3.3:1.

In the methods described herein, the amount of the composition of (a) a compound of formula (I) or a compound of formula (II), or an agriculturally acceptable salt or ester thereof, and (b) one or more of copper salts, diquat dibromide, endothal, or fluridone, or agriculturally acceptable salts or esters thereof applied to a body of water to be treated can be applied in a concentrated form such that the final dilution level of the composition of (a) a compound of formula (I) or a compound of formula (II), or an agriculturally acceptable salt or ester thereof, and (b) one or more of copper salts, diquat dibromide, endothal, or fluridone, or agriculturally acceptable salts or esters thereof is between 0.25 parts-per-billion (ppb) and 30,000 ppb. Additionally in the methods described herein, the amount of the composition of (a) a compound of formula (I) or a compound of formula (II), or an agriculturally acceptable salt or ester thereof, and (b) one or more of copper salts, diquat dibromide, endothal, or fluridone, or agriculturally acceptable salts or esters thereof applied to a body of water to be treated can be applied in a concentrated form such that the final dilution level of the composition of (a) a compound of formula (I) or a compound of formula (II), or an agriculturally acceptable salt or ester thereof, and (b) one or more of copper salts, diquat dibromide, endothal, or fluridone, or agriculturally acceptable salts or esters thereof is between 0.25 ppb and 30,000 ppb, 0.25 ppb and 25,000 ppb, 0.25 ppb and 20,000 ppb, 0.25 ppb and 15,000 ppb, 0.25 ppb and 10,000 ppb, 0.25 ppb and 8000 ppb, 0.25 ppb and 6000 ppb, 0.25 ppb and 5000 ppb, 0.25 ppb and 4000 ppb, 0.25 ppb and 3000 ppb, 0.25 ppb and 2000 ppb, 0.25 ppb and 1500 ppb, 0.25 ppb and 1250 ppb, 0.25 ppb and 1000 ppb, 0.25 ppb and 900 ppb, 0.25 ppb and 800 ppb, 0.25 ppb and 700 ppb, 0.25 ppb and 600 ppb, 0.25 ppb and 500 ppb, 0.25 ppb and 450 ppb, 0.25 ppb and 400 ppb, 0.25 ppb and 375 ppb, 0.25 ppb and 350 ppb, 0.25 ppb and 325 ppb, 0.25 ppb and 300 ppb, 0.25 ppb and 275 ppb, 0.25 ppb and 250 ppb, 0.25 ppb and 225 ppb, 0.25 ppb and 200 ppb, 0.25 ppb and 190 ppb, 0.25 ppb and 180 ppb, 0.25 ppb and 170 ppb, 0.25 ppb and 160 ppb, 0.25 ppb and 150 ppb, 0.25 ppb and 140 ppb, 0.25 ppb and 130 ppb, 0.25 ppb and 120 ppb, 0.25 ppb and 110 ppb, 0.25 ppb and 100 ppb, 0.25 ppb and 90 ppb, 0.25 ppb and 80 ppb, 0.25 ppb and 70 ppb, 0.25 ppb and 60 ppb, 0.25 ppb and 50 ppb, 0.25 ppb and 40 ppb, 0.25 ppb and 30 ppb, 0.25 ppb and 20 ppb, and 0.25 ppb and 10 ppb; 1 ppb and 30,000 ppb, 1 ppb and 25,000 ppb, 1 ppb and 20,000 ppb, 1 ppb and 15,000 ppb, 1 ppb and 10,000 ppb, 1 ppb and 8000 ppb, 1 ppb and 6000 ppb, 1 ppb and 4000 ppb, 1 ppb and 2000 ppb, 1 ppb and 1000 ppb, 1 ppb and 500 ppb, 1 ppb and 200 ppb, 1 ppb and 150 ppb, 1 ppb and 100 ppb, 1 ppb and 90 ppb, 1 ppb and 80 ppb, 1 ppb and 70 ppb, 1 ppb and 60 ppb, 1 ppb and 50 ppb, 1 ppb and 40 ppb, 1 ppb and 30 ppb, 1 ppb and 20 ppb, and 1 ppb and 10 ppb; 5 ppb and 30,000 ppb, 5 ppb and 25,000 ppb, 5 ppb and 20,000 ppb, 5 ppb and 15,000 ppb, 5 ppb and 10,000 ppb, 5 ppb and 8000 ppb, 5 ppb and 6000 ppb, 5 ppb and 4000 ppb, 5 ppb and 2000 ppb, 5 ppb and 1000 ppb, 5 ppb and 800 ppb, 5 ppb and 500 ppb, 5 ppb and 350 ppb, 5 ppb and 350 ppb, 5 ppb and 200 ppb, 5 ppb and 150 ppb, 5 ppb and 100 ppb, 5 ppb and 90 ppb, 5 ppb and 80 ppb, 5 ppb and 70 ppb, 5 ppb and 60 ppb, 5 ppb and 50 ppb, 5 ppb and 40 ppb, 5 ppb and 30 ppb, 5 ppb and 20 ppb, and 5 ppb and 10 ppb; 10 ppb and 30,000 ppb, 10 ppb and 25,000 ppb, 10 ppb and 20,000 ppb, 10 ppb and 15,000 ppb, 10 ppb and 10,000 ppb, 10 ppb and 8000 ppb, 10 ppb and 6000 ppb, 10 ppb and 4000 ppb, 10 ppb and 2000 ppb, 10 ppb and 1000 ppb, 10 ppb and 500 ppb, 10 ppb and 250 ppb, 10 ppb and 200 ppb, 10 ppb and 150 ppb, 10 ppb and 100 ppb, 10 ppb and 90 ppb, 10 ppb and 80 ppb, 10 ppb and 70 ppb, 10 ppb and 60 ppb, 10 ppb and 50 ppb, 10 ppb and 40 ppb, 10 ppb and 30 ppb, and 10 ppb and 20 ppb; 20 ppb and 30,000 ppb, 20 ppb and 25,000 ppb, 20 ppb and 20,000 ppb, 20 ppb and 15,000 ppb, 20 ppb and 10,000 ppb, 20 ppb and 8000 ppb, 20 ppb and 6000 ppb, 20 ppb and 4000 ppb, 20 ppb and 2000 ppb, 20 ppb and 1000 ppb, 20 ppb and 500 ppb, 20 ppb and 250 ppb, 20 ppb and 200 ppb, 20 ppb and 150 ppb, 20 ppb and 100 ppb, 20 ppb and 90 ppb, 20 ppb and 80 ppb, 20 ppb and 70 ppb, 20 ppb and 60 ppb, 20 ppb and 50 ppb, 20 ppb and 40 ppb, and 20 ppb and 30 ppb; 30 ppb and 30,000 ppb, 30 ppb and 25,000 ppb, 30 ppb and 20,000 ppb, 30 ppb and 15,000 ppb, 30 ppb and 10,000 ppb, 30 ppb and 8000 ppb, 30 ppb and 6000 ppb, 30 ppb and 4000 ppb, 30 ppb and 2000 ppb, 30 ppb and 1000 ppb, 30 ppb and 500 ppb, 30 ppb and 250 ppb, 30 ppb and 200 ppb, 30 ppb and 150 ppb, 30 ppb and 100 ppb, 30 ppb and 90 ppb, 30 ppb and 80 ppb, 30 ppb and 70 ppb, 30 ppb and 60 ppb, 30 ppb and 50 ppb, and 30 ppb and 40 ppb; 40 ppb and 30,000 ppb, 40 ppb and 25,000 ppb, 40 ppb and 20,000 ppb, 40 ppb and 15,000 ppb, 40 ppb and 10,000 ppb, 40 ppb and 8000 ppb, 40 ppb and 6000 ppb, 40 ppb and 4000 ppb, 40 ppb and 2000 ppb, 40 ppb and 1000 ppb, 40 ppb and 500 ppb, 40 ppb and 325 ppb, 40 ppb and 250 ppb, 40 ppb and 200 ppb, 40 ppb and 150 ppb, 40 ppb and 100 ppb, 40 ppb and 90 ppb, 40 ppb and 80 ppb, 40 ppb and 70 ppb, 40 ppb and 60 ppb, and 40 ppb and 50 ppb; 50 ppb and 30,000 ppb, 50 ppb and 25,000 ppb, 50 ppb and 20,000 ppb, 50 ppb and 15,000 ppb, 50 ppb and 10,500, 50 ppb and 10,000 ppb, 50 ppb and 8000 ppb, 50 ppb and 6000 ppb, 50 ppb and 4000 ppb, 50 ppb and 2000 ppb, 50 ppb and 1000 ppb, 50 ppb and 500 ppb, 50 ppb and 250 ppb, 50 ppb and 200 ppb, 50 ppb and 150 ppb, 50 ppb and 100 ppb, 50 ppb and 90 ppb, 50 ppb and 80 ppb, 50 ppb and 70 ppb, and 50 ppb and 60 ppb; 75 ppb and 30,000 ppb, 75 ppb and 25,000 ppb, 75 ppb and 20,000 ppb, 75 ppb and 15,000 ppb, 75 ppb and 10,000 ppb, 75 ppb and 8000 ppb, 75 ppb and 6000 ppb, 75 ppb and 4000 ppb, 75 ppb and 2000 ppb, 75 ppb and 1000 ppb, 75 ppb and 500 ppb, 75 ppb and 250 ppb, 75 ppb and 200 ppb, 75 ppb and 150 ppb, 75 ppb and 100 ppb, 75 ppb and 90 ppb, and 75 ppb and 80 ppb; 100 ppb and 30,000 ppb, 100 ppb and 25,000 ppb, 100 ppb and 20,000 ppb, 100 ppb and 15,000 ppb, 100 ppb and 10,000 ppb, 100 ppb and 8000 ppb, 100 ppb and 6000 ppb, 100 ppb and 4000 ppb, 100 ppb and 2000 ppb, 100 ppb and 1000 ppb, 100 ppb and 500 ppb, 100 ppb and 250 ppb, 100 ppb and 200 ppb, 100 ppb and 150 ppb, 100 ppb and 125 ppb, 100 ppb and 110 ppb, 200 ppb and 10,000 ppb, 250 ppb and 2500 ppb, 333 ppb and 1000 ppb, 700 ppb and 28,500 ppb, 900 ppb and 7,500 ppb, 1,100 ppb and 9,000 ppb, and 2,100 ppb and 8,500 ppb. Additionally, the amount of (a) a compound of formula (I) or a compound of formula (II), or an agriculturally acceptable salt or ester thereof, applied to a body of water to be treated can be applied in a concentrated form such that the final dilution level of (a) a compound of formula (I) or a compound of formula (II), or an agriculturally acceptable salt or ester thereof, is 0.1 ppb, 0.25 ppb, 0.5 ppb, 1 ppb, 2 ppb, 3 ppb, 4 ppb, 5 ppb, 6 ppb, 7 ppb, 8 ppb, 9 ppb, 10 ppb, 12 ppb, 14 ppb, 16 ppb, 18 ppb, 20 ppb, 22 ppb, 24 ppb, 26 ppb, 28 ppb, 30 ppb, 32 ppb, 34 ppb, 36 ppb, 38 ppb, 40 ppb, 42 ppb, 44 ppb, 46 ppb, 48 ppb, 50 ppb, 55 ppb, 60 ppb, 65 ppb, 70 ppb, 75 ppb, 80 ppb, 85 ppb, 90 ppb, 95 ppb, 100 ppb, 110 ppb, 120 ppb, 130 ppb, 140 ppb, 150 ppb, 160 ppb, 170 ppb, 180 ppb, 190 ppb, 200 ppb, 220 ppb, 240 ppb, 260 ppb, 280 ppb, 300 ppb, 320 ppb, 340 ppb, 360 ppb, 380 ppb, 400 ppb, 420 ppb, 440 ppb, 460 ppb, 480 ppb, 500 ppb, 600 ppb, 700 ppb, 800 ppb, 900 ppb or 1,000 ppb, and the amount of (b) one or more of copper salts, diquat dibromide, endothal, or fluridone, or agriculturally acceptable salts or esters thereof applied to a body of water to be treated can be applied in a concentrated form such that the final dilution level of (b) one or more of copper salts, diquat dibromide, endothal, or fluridone, or agriculturally acceptable salts or esters thereof can be 0.1 ppb, 0.25 ppb, 0.5 ppb, 1 ppb, 2 ppb, 3 ppb, 4 ppb, 5 ppb, 6 ppb, 7 ppb, 8 ppb, 9 ppb, 10 ppb, 12 ppb, 14 ppb, 16 ppb, 18 ppb, 20 ppb, 22 ppb, 24 ppb, 26 ppb, 28 ppb, 30 ppb, 32 ppb, 34 ppb, 36 ppb, 38 ppb, 40 ppb, 42 ppb, 44 ppb, 46 ppb, 48 ppb, 50 ppb, 55 ppb, 60 ppb, 65 ppb, 70 ppb, 75 ppb, 80 ppb, 85 ppb, 90 ppb, 95 ppb, 100 ppb, 110 ppb, 120 ppb, 130 ppb, 140 ppb, 150 ppb, 160 ppb, 170 ppb, 180 ppb, 190 ppb, 200 ppb, 220 ppb, 240 ppb, 260 ppb, 280 ppb, 300 ppb, 320 ppb, 340 ppb, 360 ppb, 380 ppb, 400 ppb, 420 ppb, 440 ppb, 460 ppb, 480 ppb, 500 ppb, 550 ppb, 600 ppb, 650 ppb, 700 ppb, 750 ppb, 800 ppb, 850 ppb, 900 ppb, 950 ppb, 1000 ppb, 1500 ppb, 2000 ppb, 2500 ppb, 3000 ppb, 3500 ppb, 4000 ppb, 4500 ppb, 5000 ppb, 5500 ppb, 6000 ppb, 6500 ppb, 7000 ppb, 7500 ppb, 8000 ppb, 8500 ppb, 9000 ppb, 9500 ppb, 10,000 ppb, 15,000 ppb, 20,000 ppb, 25,000 ppb or 30,000 ppb.

In other examples of the methods described herein, the amount of (a) a compound of formula (I) or a compound of formula (II), or an agriculturally acceptable salt or ester thereof, applied to a body of water to be treated can be applied in a concentrated form such that the final dilution level of (a) a compound of formula (I) or a compound of formula (II), or an agriculturally acceptable salt or ester thereof, is less than 1,000 ppb. In another example of the methods described herein, the amount of (a) a compound of formula (I) or a compound of formula (II), or an agriculturally acceptable salt or ester thereof, applied to a body of water to be treated can be applied in a concentrated form such that the final dilution level of (a) a compound of formula (I) or a compound of formula (II), or an agriculturally acceptable salt or ester thereof, is less than 0.25 ppb, less than 1 ppb, less than 2 ppb, less than 3 ppb, less than 4 ppb, less than 5 ppb, less than 6 ppb, less than 7 ppb, less than 8 ppb, less than 9 ppb, less than 10 ppb, less than 12 ppb, less than 14 ppb, less than 16 ppb, less than 18 ppb, less than 20 ppb, less than 22 ppb, less than 24 ppb, less than 26 ppb, less than 28 ppb, less than 30 ppb, less than 32 ppb, less than 34 ppb, less than 36 ppb, less than 38 ppb, less than 40 ppb, less than 42 ppb, less than 44 ppb, less than 46 ppb, less than 48 ppb, less than 50 ppb, less than 55 ppb, less than 60 ppb, less than 65 ppb, less than 70 ppb, less than 75 ppb, less than 80 ppb, less than 85 ppb, less than 90 ppb, less than 95 ppb, less than 100 ppb, less than 110 ppb, less than 120 ppb, less than 130 ppb, less than 140 ppb, less than 150 ppb, less than 160 ppb, less than 170 ppb, less than 180 ppb, less than 190 ppb, less than 200 ppb, less than 210 ppb, less than 220 ppb, less than 230 ppb, less than 240 ppb, less than 250 ppb, less than 275 ppb, less than 300 ppb, less than 325 ppb, less than 350 ppb, less than 400 ppb, less than 450 ppb, less than 500 ppb, less than 550 ppb, less than 600 ppb, less than 650 ppb, less than 700 ppb, less than 750 ppb, less than 800 ppb, less than 850 ppb, less than 900 ppb, less than 950 ppb, or less than 1000 ppb.

In other examples of the methods described herein, the amount of the composition of (a) a compound of formula (I) or a compound of formula (II), or an agriculturally acceptable salt or ester thereof, and (b) one or more of copper salts, diquat dibromide, endothal, or fluridone, or agriculturally acceptable salts or esters thereof to a body of water to be treated can be applied in a concentrated form either in a tank-mix, sequentially, or in a pre-mix such that the final dilution level of the composition of (a) a compound of formula (I) or a compound of formula (II), or an agriculturally acceptable salt or ester thereof, and (b) one or more of copper salts, diquat dibromide, endothal, or fluridone, or agriculturally acceptable salts or esters thereof is less than 30,000 ppb. In additional examples of the methods described herein, the amount of the composition of (a) a compound of formula (I) or a compound of formula (II), or an agriculturally acceptable salt or ester thereof, and (b) one or more of copper salts, diquat dibromide, endothal, or fluridone, or agriculturally acceptable salts or esters thereof applied to a body of water to be treated can be applied in a concentrated form such that the final dilution level of the composition of (a) a compound of formula (I) or a compound of formula (II), or an agriculturally acceptable salt or ester thereof, and (b) one or more of copper salts, diquat dibromide, endothal, or fluridone, or agriculturally acceptable salts or esters thereof is less than 0.25 ppb, less than 1 ppb, less than 2 ppb, less than 3 ppb, less than 4 ppb, less than 5 ppb, less than 6 ppb, less than 7 ppb, less than 8 ppb, less than 9 ppb, less than 10 ppb, less than 12 ppb, less than 14 ppb, less than 16 ppb, less than 18 ppb, less than 20 ppb, less than 22 ppb, less than 24 ppb, less than 26 ppb, less than 28 ppb, less than 30 ppb, less than 32 ppb, less than 34 ppb, less than 36 ppb, less than 38 ppb, less than 40 ppb, less than 42 ppb, less than 44 ppb, less than 46 ppb, less than 48 ppb, less than 50 ppb, less than 55 ppb, less than 60 ppb, less than 65 ppb, less than 70 ppb, less than 75 ppb, less than 80 ppb, less than 85 ppb, less than 90 ppb, less than 95 ppb, less than 100 ppb, less than 110 ppb, less than 120 ppb, less than 130 ppb, less than 140 ppb, less than 150 ppb, less than 160 ppb, less than 170 ppb, less than 180 ppb, less than 190 ppb, less than 200 ppb, less than 210 ppb, less than 220 ppb, less than 230 ppb, less than 240 ppb, less than 250 ppb, less than 275 ppb, less than 300 ppb, less than 325 ppb, less than 350 ppb, less than 400 ppb, less than 450 ppb, less than 500 ppb, less than 550 ppb, less than 600 ppb, less than 650 ppb, less than 700 ppb, less than 750 ppb, less than 800 ppb, less than 850 ppb, less than 900 ppb, less than 950 ppb, less than 1000 ppb, less than 1100 ppb, less than 1200 ppb, less than 1300 ppb, less than 1400 ppb, less than 1500 ppb, less than 1600 ppb, less than 1700 ppb, less than 1800 ppb, less than 1900 ppb, less than 2000 ppb, less than 2500 ppb, less than 3000 ppb, less than 3500 ppb, less than 4000 ppb, less than 4500 ppb, less than 5000 ppb, less than 6000 ppb, less than 7000 ppb, less than 8000 ppb, less than 9000 ppb, less than 10,000 ppb, less than 12,500 ppb, less than 15,000 ppb, less than 17,500 ppb, less than 20,000 ppb, less than 25,000 ppb, or less than 30,000 ppb.

As described herein, the composition of (a) a compound of formula (I) or a compound of formula (II), or an agriculturally acceptable salt or ester thereof, and (b) one or more of copper salts, diquat dibromide, endothal, or fluridone, or agriculturally acceptable salts or esters thereof is unexpectedly effective when applied to aquatic plants at very low concentrations. This unexpected effectiveness can be used to improve selectivity for target aquatic weeds, thus having a lesser effect on non-target plant species due to reduced concentration of or exposure to the herbicidal agents.

B. Other Actives

The mixtures described herein can be applied in conjunction with one or more other herbicides to control a wider variety of undesirable vegetation. When used in conjunction with other herbicides, the composition can be formulated with the other herbicide or herbicides, tank-mixed with the other herbicide or herbicides or applied sequentially with the other herbicide or herbicides. Some of the herbicides that can be employed in conjunction with the compositions and methods described herein include, but are not limited to acid, salt, choline salt, ester and optically active isomer forms of the following herbicides: 4-CPA, 4-CPB, 4-CPP, 3,4-DA, 2,4-D, 2,4-D choline salt, 2,4-DB, 3,4-DB, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, bentazon, benthiocarb, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone (e.g., carfentrazone-ethyl), CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon (e.g., cinidon-ethyl), cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, CPMF, CPPC, credazine, cresol, cumyluron, cyanatryn, cyanazine, cycloate, cyclopyrimorate, cyclosulfamuron, cycloxydim, cycluron, cyhalofop (e.g., cyhalofop-butyl), cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, disul, dithiopyr, diuron, DMPA, DNOC, DSMA, EBEP, eglinazine, epronaz, EPTC, erbon, esprocarb, ethbenzamide, ethalfluralin, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop (e.g., fenoxaprop-P-ethyl), fenoxaprop-P-ethyl+isoxadifen-ethyl, fenoxasulfone, fenquinotrione, fenteracol, fenthiaprop, fentrazamide, fenuron, ferrous sulfate, flamprop, flamprop-M, flazasulfuron, florasulam, fluazifop (e.g., fluazifop-P-butyl), fluazolate, flucarbazone, flucetosulfuron, fluchloralin, flufenacet, flufenican, flufenpyr (e.g., flufenpyr-ethyl), flumetsulam, flumezin, flumiclorac (e.g., flumiclorac-pentyl), flumioxazin, flumipropyn, fluometuron, fluorodifen, fluoroglycofen, fluoromidine, fluoronitrofen, fluothiuron, flupoxam, flupropacil, flupropanate, flupyrsulfuron, flurochloridone, fluroxypyr, flurtamone, fluthiacet, fomesafen, foramsulfuron, fosamine, fumiclorac, furyloxyfen, halosafen, halosulfuron (e.g., halosulfuron-methyl), haloxydine, haloxyfop-methyl, haloxyfop-P (e.g., haloxyfop-P-methyl), hexachloroacetone, hexaflurate, hexazinone, imazamethabenz, imazamox, imazapic, imazapyr, imazaquin, imazosulfuron, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lancotrione, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufenethyl, parafluron, paraquat, pebulate, pelargonic acid, pendimethalin, penoxsulam, pentachlorophenol, pentanochlor, pentoxazone, perfluidone, pethoxamid, phenisopham, phenmedipham (e.g., phenmedipham-ethyl), phenobenzuron, phenylmercury acetate, picloram, picolinafen, pinoxaden, piperophos, potassium arsenite, potassium azide, potassium cyanate, pretilachlor, primisulfuron (e.g., primisulfuron-methyl), procyazine, prodiamine, profluazol, profluralin, profoxydim, proglinazine, prohexadione-calcium, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen (e.g., pyraflufen-ethyl), pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazonemethyl, thifensulfuron, thifensulfuron-methyl, thiobencarb, tiafenacil, tiocarbazil, tioclorim, tolpyralate, topramezone, tralkoxydim, triafamone, tri-allate, triasulfuron, triaziflam, tribenuron (e.g., tribenuron-methyl), tricamba, triclopyr (e.g., triclopyr choline salt), triclopyr esters and salts, tridiphane, trietazine, trifloxysulfuron, trifludimoxazin, trifluralin, triflusulfuron, trifop, trifopsime, trihydroxytriazine, trimeturon, tripropindan, tritac, tritosulfuron, vernolate, xylachlor, and salts, choline salts, esters, optically active isomers and mixtures thereof.

Exemplary additional pesticides include, but are not limited to, flumioxazin, carfentrazone-ethyl, aminopyralid, topramezone, 2,4-D, 2,4-D choline salt, triclopyr, triclopyr choline salt, penoxsulam, imazamox, and bispyribac-sodium, including, with respect to the carboxylic acid containing pesticides, agriculturally acceptable salts or esters thereof.

C. Safeners

The compositions described herein can be employed in combination with one or more herbicide safeners, such as AD-67 (MON 4660), benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, R29148 and N-phenyl-sulfonylbenzoic acid amides, to enhance their selectivity to non-target aquatic plants.

D. Adjuvants/Carriers

The compositions provided herein can further comprise at least one or more agriculturally acceptable adjuvant or carrier. Suitable adjuvants or carriers should not be phytotoxic to valuable plant species, particularly at the concentrations employed in applying the compositions for selective aquatic weed control, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank-mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99; paraffinic oil, alkoxylated alcohol non-ionic surfactant; mineral oil, surfactant blend.

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, water is the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

The compositions described herein can further comprise one or more surface-active agents. Such surface-active agents are employed in both solid and liquid compositions, and in certain cases those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in *McCutcheon's Detergents and Emulsifiers Annual*, MC Publishing Corporation: Ridgewood, N J, 1998 and in *Encyclopedia of Surfactants, Vol. I-III*, Chemical Publishing Company: New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide additionproducts, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and methyl esters.

These materials, such as vegetable or seed oils and their esters, can be used interchangeably as an agricultural adjuvant, as a liquid carrier or as a surface active agent.

Other exemplary additives for use in the compositions provided herein include, but are not limited to, compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

III. Methods of Use

Methods of controlling aquatic weeds in a body of water, include providing in the body of water a composition containing a herbicidally effective amount of (a) a compound of formula (I) or a compound of formula (II),

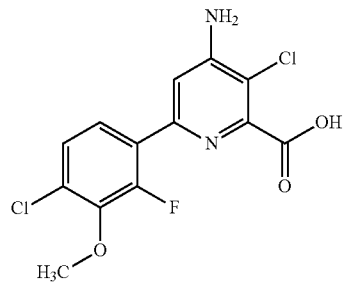

(I)

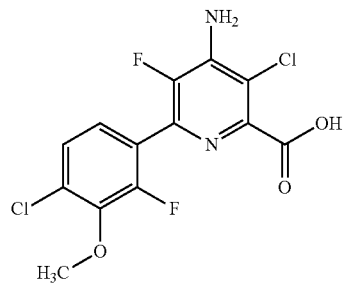

(II)

or an agriculturally acceptable salt or ester thereof, and (b) one or more of copper salts, diquat dibromide, endothal, or fluridone, or agriculturally acceptable salts or esters thereof.

Herbicidal activity is exhibited by the compounds when they are applied to the body of water containing the plants to be controlled at any stage of growth. The effect observed depends upon the plant species to be controlled, the stage of growth of the plant, the application parameters of dilution, the particle size of solid components, the environmental conditions at the time of use, the specific compound employed, the specific adjuvants and carriers employed, and the like, as well as the amount of chemical applied. These and other factors can be adjusted to promote herbicidal action. In the present methods, the compositions described herein are applied to relatively immature and mature undesirable vegetation to achieve the maximum control of weeds.

The composition of (a) a compound of formula (I) or a compound of formula (II), or an agriculturally acceptable salt or ester thereof, and (b) one or more of diquat dibromide, copper salts, endothal, or fluridone, or agriculturally acceptable salts or esters thereof and complementary herbicides is applied at the same time, either as a combination formulation or as a tank-mix, or as a sequential application.

In the methods described herein, the composition of (a) a compound of formula (I) or a compound of formula (II), or an agriculturally acceptable salt or ester thereof, and (b) one or more of copper salts, diquat dibromide, endothal, or fluridone, or agriculturally acceptable salts or esters thereof can be provided in (e.g., applied to) a body of water to be treated by the use of conventional dusters, sprayers, injectors and granule applicators, by addition to injection water, and by other conventional means known to those skilled in the art.

The methods and compositions of the invention may also be used in the complete or partial control of many emerged, floating, immersed, and submersed aquatic plants and shoreline grasses. For example, the floating plants include but are not limited to common duckweed (*Lemna minor*), limnophila (*Limnophila sessiliflora*), frog's bit (*Limnobium spongia*), mosquito fern (*Azoila caroliniana*), water fern (*Salvinia* minima and *S. molesta*), salvinia (*Salvinia* spp.), water hyacinth (*Eichhornia crassipes*), water lettuce (*Pistia stratiotes*) and common watermeal (*Woffia columbiana*); the immersed plants include but are not limited to spatterdock (*Nuphar luteum*), water-lily (*Nymphaea* spp.), alligatorweed (*Alternanthera philoxeroides*), American lotus (*Nelumbo lutea*), cattail (*Typha* spp.), creeping waterprimrose (*Ludwigia peploides*), parrotfeather (*Myriophyllum aquaticum*), smartweed (*Polygonum* spp.), spikerush (*Eleocharis* spp.), waterpurslane (*Ludwigia palustris*), water pennywort (*Hydrocotyle umbellate*), floating heart (*Nymphoides* spp.), bulrush (*Schoenoplectus* spp.), lanceleaf pickerelweed (*Pontederia* spp.), arrowhead (*Sagittaria* spp.) and watershield (*Brasenia schreberi*); the submersed plants include but are not limited to bladderwart (*Utricularia* spp.), baby's tears (*Micranthemum* spp.), common coontail (*Ceratophyllum demersum*), common elodea (*Elodea canadensis*), Brazilian elodea (*Egeria densa*), fanwort (*Cabomba caroliniana*), hydrilla (*Hydrilla verticillata*), naiad (*Najas* spp.), pondweed (*Potamogeton* spp.) and more specifically curlyleaf pondweed (*Potamogeton crispus*) and Illinois pondweed (*P. illinoensis*), horned pondweed (*Zannichellia palustris*), bacopa (*Bacopa* spp.), watermilfoil (*Myriophyllum* spp.) including Eurasian watermilfoil (*M. spicatum*), tapegrass or American eelgrass (*Vallisneria americana*), and variable leaf watermilfoil (*Myriophyllum heterophyllum*); and the shoreline grasses barnyardgrass (*Echinochloa crus-galli*), and southern watergrass (*Hydrochloa caroliniensis*). Particularly preferred plant types for control in accordance with the methods described herein include *hydrilla*, Eurasian watermilfoil, curlyleaf pondweed, alligatorweed, yellow nutsedge, barnyardgrass, early watergrass, *Echinochloa* species, saramollagrass, and Chinese sprangletop.

Bodies of water to be treated using the methods described herein will typically be fresh water bodies such as ponds, lakes, wet lands, reservoirs, rivers, streams, canals, ditches or irrigation canals, although other bodies of water may also be treated in accordance with the methods. The methods described herein may be used in bodies of water that include rice paddies or rice fields and any water containment system including, but not limited to, water storage, water cooling, water heating, and the like.

The compositions and methods described herein may be used to control herbicide resistant or tolerant weeds. Exemplary resistant or tolerant weeds include, but are not limited to, biotypes resistant or tolerant to acetolactate synthase (ALS) or acetohydroxy acid synthase (AHAS) inhibitors (e.g., imidazolinones, sulfonylureas, pyrimidinylthiobenzoates, dimethoxy-pyrimidines, triazolopyrimidine sulfonamides, and sulfonylaminocarbonyltriazolinones), photosystem II inhibitors (e.g., phenylcarbamates, pyridazinones, triazines, triazinones, uracils, amides, ureas, benzothiadiazinones, nitriles, and phenylpyridazines), acetyl CoA carboxylase (ACCase) inhibitors (e.g., aryloxyphenoxypropionates, cyclohexanediones, and phenylpyrazolines), synthetic auxins (e.g., benzoic acids, phenoxycarboxylic acids, pyridine carboxylic acids (e.g., arylpicolinates and aminopyrimidines), and quinoline carboxylic acids), auxin transport inhibitors (e.g., phthalamates and semicarbazones), photosystem I inhibitors (e.g., bipyridyliums), 5-enolpyruvylshikimate-3-phosphate (EPSP) synthase inhibitors (e.g., glyphosate), glutamine synthetase inhibitors (e.g., glufosinate and bialafos), microtubule assembly inhibitors (e.g., benzamides, benzoic acids, dinitroanilines, phosphoramidates, and pyridines), mitosis inhibitors (e.g., carbamates), very long chain fatty acid (VLCFA) inhibitors (e.g., acetamides, chloroacetamides, oxyacetamides, and tetrazolinones), fatty acid and lipid synthesis inhibitors (e.g., phosphorodithioates, thiocarbamates, benzofuranes, and chlorocarbonic acids), protoporphyrinogen oxidase (PPO) inhibitors (e.g., diphenylethers, N-phenylphthalimides, oxadiazoles, oxazolidinediones, phenylpyrazoles, pyrimidinediones, thiadiazoles, and triazolinones), carotenoid biosynthesis inhibitors (e.g., clomazone, amitrole, aclonifen, and fluridone), phytoene desaturase (PDS) inhibitors (e.g., amides, anilidex, furanones, phenoxybutan-amides, pyridiazinones, and pyridines), 4-hydroxyphenyl-pyruvate-dioxygenase (HPPD) inhibitors (e.g., callistemones, isoxazoles, pyrazoles, and triketones), cellulose biosynthesis inhibitors (e.g., nitriles, benzamides, quinclorac, and triazolocarboxamides), herbicides with multiple modes-of-action such as quinclorac, and unclassified herbicides such as arylaminopropionic acids, difenzoquat, and organoarsenicals. Exemplary resistant or tolerant weeds include, but are not limited to, biotypes with resistance or tolerance to single or multiple herbicides, biotypes with resistance or tolerance to single or multiple chemical classes, biotypes with resistance or tolerance to single or multiple herbicide modes-of-action, and biotypes with single or multiple resistance or tolerance mechanisms (e.g., target site resistance, non-target site based resistance, metabolic resistance or a combination of target site, non-target site, or metabolic resistance).

In the methods and compositions described herein the herbicidally active ingredients should be maintained at herbicidally effective levels in the body of water in contact with the targeted plant to achieve control. Thus, in accordance with methods described herein, the herbicidal agents will be maintained in the treatment area or body of water under treatment for about 1 to 4 weeks, and preferably for at least about four weeks, and more preferably in the range of about four to sixteen weeks or more. The concentration of the herbicidal agent may be maintained through the use of sequential or bump treatments, or continuous injection, using the same agent. The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Example 1

Greenhouse Evaluation of In-Water Applied Herbicidal Activity in a Flooded Pot System Weed seeds, nutlets, or vegetative cuttings of the desired test plant species were planted in puddled soil (mud) prepared by mixing a shredded, non-sterilized mineral soil (50.5 percent silt, 25.5 percent clay, and 24 percent sand, with a pH of approximately 7.6 and an organic matter content of approximately 2.9 percent) and water at a 1:1 volumetric ratio. The prepared mud was dispensed in 365 milliliter (mL) aliquots into 480 mL non-perforated plastic pots with a surface area of 86.59 square centimeters ($cm^2$) leaving a headspace of 3 centimeters (cm) in each pot. Mud was allowed to dry overnight prior to planting or transplanting.

The aquatic environment was created by filling the 3 cm headspace of the pots with water. When required to ensure good germination and healthy plants, a fungicide treatment and/or other chemical or physical treatment was applied. The plants were grown for 4-20 days in a greenhouse with an approximate 14 hour (h) photoperiod which was maintained at about 29° C. during the day and about 26° C. during the night. Nutrients were added as Osmocote® (19:6:12, N:P:K+minor nutrients) at 2 grams (g) per 480 mL pot. Water was added on a regular basis to maintain the paddy flood, and supplemental lighting was provided with overhead metal halide 1000-Watt lamps as necessary. The plants were employed for testing when they reached the second through fifth true leaf stage or $5^{th}$ node stage.

Treatments consisted of the benzyl ester of 4-amino-3-chloro-5-fluoro-6-(4-chloro-2-fluoro-3-methoxy-phenyl) pyridine-2-carboxylic acid (Compound II) formulated as a suspension concentrate (SC) and various herbicidal components alone and in combination. Compound II was applied on an active ingredient (ai) basis. Other herbicidal components included copper sulfate pentahydrate (as 99% weight per weight (w/w) copper sulfate granular crystals); mixed copper ethanolamine complex (as Cutrine® Plus Granular); endothal (as the mono (N,N-dimethylalkylamine) salt of endothal or Hydrothol® Granular, 5% w/w acid equivalent (ae), 11.2% w/w active ingredient (ai)); fluridone (as Sonar® A.S., 41.7% w/w ai); and diquat (as diquat dibromide or Weedtrine®-D, 8.53% w/w ai).

Treatment requirements for each compound or herbicidal component were calculated based upon the rates being tested, the concentration of active ingredient or acid equivalent in the formulation, and a treatment application volume of 2 mL per compound per pot.

Measured amounts of formulated compounds were placed in individual glass vials and were dissolved in an aliquot of an aqueous mixture containing 1.25% volume per volume (v/v) Agri-Dex® crop oil concentrate. A stock solution was prepared for each treatment concentration. Applications were made by injecting an appropriate amount of the application solution into the aqueous layer of the flooded greenhouse pot. Control plants were treated in the same manner with the solvent blank.

The treated plants and control plants were placed in a greenhouse as described above and water was added as needed to maintain a flood in the pot. After approximately 20 days after application (DAA), the condition of the test plants, compared with that of the untreated plants, was determined visually and scored on a scale of 0 to 100 percent where 0 corresponds to no injury or growth reduction and 100 corresponds to complete kill.

The compounds tested, application rates employed, plant species tested, and results are given in Tables 1-5.

TABLE 1

Activity of In-Water Herbicidal Compounds in a Flooded Pot System (20 DAA) in the Greenhouse.

| Weed Bayer Code | % Submerged | Compound II | | Copper Sulfate | | Combination | |
|---|---|---|---|---|---|---|---|
| | | | | | | Measured | Colby Predicted |
| | | ppb | Mean % Weed Control | ppb | Mean % Weed Control | Mean % Weed Control | Mean % Weed Control |
| CYPES | 4 lf (30%) | 33.25 | 18.0 | 300 | 0.0 | 40.0 | 18.0 |
| CYPES | 4 lf (30%) | 66.6 | 68.0 | 300 | 0.0 | 100.0 | 68.0 |
| CYPES | 4 lf (30%) | 33.25 | 18.0 | 600 | 0.0 | 70.0 | 18.0 |
| CYPES | 4 lf (30%) | 66.6 | 68.0 | 600 | 0.0 | 100.0 | 68.0 |
| ALRPH | 5 node | 33.25 | 55.0 | 300 | 0.0 | 70.0 | 55.0 |
| ALRPH | 5 node | 66.6 | 68.0 | 300 | 0.0 | 80.0 | 68.0 |
| ALRPH | 5 node | 33.25 | 55.0 | 600 | 0.0 | 70.0 | 55.0 |
| ALRPH | 5 node | 66.6 | 68.0 | 600 | 0.0 | 83.0 | 68.0 |
| ALRPH | 5 node | 33.25 | 55.0 | 900 | 0.0 | 65.0 | 55.0 |

TABLE 2

Activity of In-Water Herbicidal Compounds in a Flooded Pot System (20 DAA) in the Greenhouse.

| Weed Bayer Code | % Submerged | Compound II ppb | Compound II Mean % Weed Control | Mixed Copper Ethanolamine Complex* ppb | Mixed Copper Ethanolamine Complex* Mean % Weed Control | Combination Measured Mean % Weed Control | Combination Colby Predicted Mean % Weed Control |
|---|---|---|---|---|---|---|---|
| ISCRU | 2-3 lf (30-50%) | 66.6 | 75.0 | 8300 | 0.0 | 90.0 | 75.0 |
| ISCRU | 2-3 lf (30-50%) | 133.4 | 85.0 | 8300 | 0.0 | 100.0 | 85.0 |
| LEFCH | 5 lf (30%) | 66.6 | 20.0 | 4200 | 0.0 | 40.0 | 20.0 |
| LEFCH | 5 lf (30%) | 66.6 | 20.0 | 8300 | 0.0 | 40.0 | 20.0 |
| ECHCG | 2-5 lf (30%) | 33.25 | 65.0 | 2100 | 0.0 | 80.0 | 65.0 |
| ECHCG | 2-5 lf (30%) | 33.25 | 65.0 | 4200 | 0.0 | 83.0 | 65.0 |
| ECHCG | 2-5 lf (30%) | 33.25 | 65.0 | 8300 | 0.0 | 98.0 | 65.0 |
| ALRPH | 5 node | 33.3 | 55.0 | 2100 | 0.0 | 78.0 | 55.0 |
| ALRPH | 5 node | 33.3 | 55.0 | 4200 | 0.0 | 88.0 | 55.0 |
| ALRPH | 5 node | 66.6 | 68.0 | 4200 | 0.0 | 78.0 | 68.0 |
| ALRPH | 5 node | 33.3 | 55.0 | 8300 | 0.0 | 68.0 | 55.0 |
| ALRPH | 5 node | 66.6 | 68.0 | 8300 | 0.0 | 80.0 | 68.0 |

*In this study, the active ingredient was applied on an elemental copper basis.

TABLE 3

Activity of In-Water Herbicidal Compounds in a Flooded Pot System (20 DAA) in the Greenhouse.

| Weed Bayer Code | % Submerged | Compound II ppb | Compound II Mean % Weed Control | Endothal ppb | Endothal Mean % Weed Control | Combination Measured Mean % Weed Control | Combination Colby Predicted Mean % Weed Control |
|---|---|---|---|---|---|---|---|
| ISCRU | 2-3 lf (30-50%) | 66.6 | 75.0 | 1120 | 0.0 | 95.0 | 75.0 |
| ISCRU | 2-3 lf (30-50%) | 133.4 | 85.0 | 4480 | 0.0 | 95.0 | 85.0 |
| ISCRU | 2-3 lf (30-50%) | 66.6 | 75.0 | 1120 | 0.0 | 85.0 | 75.0 |
| ISCRU | 2-3 lf (30-50%) | 133.4 | 85.0 | 4480 | 0.0 | 100.0 | 85.0 |
| CYPES | 4 lf (30%) | 66.6 | 68.0 | 1120 | 0.0 | 100.0 | 68.0 |
| CYPES | 4 lf (30%) | 33.3 | 18.0 | 4480 | 0.0 | 50.0 | 18.0 |
| CYPES | 4 lf (30%) | 66.6 | 68.0 | 4480 | 0.0 | 75.0 | 68.0 |
| ALRPH | 5 node | 33.3 | 55.0 | 1120 | 0.0 | 68.0 | 55.0 |
| ALRPH | 5 node | 66.6 | 68.0 | 1120 | 0.0 | 85.0 | 68.0 |
| ALRPH | 5 node | 33.3 | 55.0 | 4480 | 0.0 | 78.0 | 55.0 |
| ALRPH | 5 node | 66.6 | 68.0 | 4480 | 0.0 | 78.0 | 68.0 |
| ALRPH | 5 node | 33.3 | 55.0 | 8960 | 0.0 | 65.0 | 55.0 |
| ALRPH | 5 node | 66.6 | 68.0 | 8960 | 0.0 | 90.0 | 68.0 |

TABLE 4

Activity of In-Water Herbicidal Compounds in a Flooded Pot System (20 DAA) in the Greenhouse.

| Weed Bayer Code | % Submerged | Compound II ppb | Compound II Mean % Weed Control | Fluridone ppb | Fluridone Mean % Weed Control | Combination Measured Mean % Weed Control | Combination Colby Predicted Mean % Weed Control |
|---|---|---|---|---|---|---|---|
| ISCRU | 2-3 lf (30-50%) | 133.4 | 85.0 | 10 | 10.0 | 100.0 | 87.0 |
| ISCRU | 2-3 lf (30-50%) | 133.4 | 85.0 | 45 | 10.0 | 97.0 | 87.0 |
| CYPES | 4 lf (30%) | 66.6 | 68.0 | 10 | 0.0 | 85.0 | 68.0 |
| CYPES | 4 lf (30%) | 66.6 | 68.0 | 45 | 0.0 | 100.0 | 68.0 |
| CYPES | 4 lf (30%) | 33.3 | 18.0 | 90 | 0.0 | 75.0 | 18.0 |
| ALRPH | 5 node | 33.3 | 55.0 | 180 | 65.0 | 95.0 | 84.0 |

TABLE 5

Activity of In-Water Herbicidal Compounds in a
Flooded Pot System (20 DAA) in the Greenhouse.

| | | Compound II | | Diquat Dibromide | | Combination Measured | Colby Predicted |
|---|---|---|---|---|---|---|---|
| Weed Bayer Code | % Submerged | ppb | Mean % Weed Control | ppb | Mean % Weed Control | Mean % Weed Control | Mean % Weed Control |
| ECHOR | 2-3 lf (20-30%) | 33.3 | 25.0 | 900 | 0.0 | 50.0 | 25.0 |
| ECHOR | 2-3 lf (20-30%) | 133.4 | 78.0 | 900 | 0.0 | 95.0 | 78.0 |
| ISCRU | 2-3 lf (30-50%) | 66.6 | 75.0 | 900 | 0.0 | 90.0 | 75.0 |
| ISCRU | 2-3 lf (30-50%) | 66.6 | 75.0 | 1800 | 0.0 | 90.0 | 75.0 |
| ISCRU | 2-3 lf (30-50%) | 133.4 | 85.0 | 1800 | 0.0 | 95.0 | 85.0 |
| ISCRU | 2-3 lf (30-50%) | 66.6 | 75.0 | 3600 | 0.0 | 95.0 | 75.0 |
| ISCRU | 2-3 lf (30-50%) | 133.4 | 85.0 | 3600 | 0.0 | 95.0 | 85.0 |
| ALRPH | 5 node | 33.3 | 55.0 | 1800 | 0.0 | 68.0 | 55.0 |
| ALRPH | 5 node | 66.6 | 68.0 | 1800 | 0.0 | 100.0 | 68.0 |
| ALRPH | 5 node | 33.3 | 55.0 | 3600 | 20.0 | 75.0 | 64.0 |
| ALRPH | 5 node | 66.6 | 68.0 | 3600 | 20.0 | 85.0 | 74.0 |
| ALRPH | 5 node | 33.3 | 55.0 | 7200 | 15.0 | 83.0 | 62.0 |
| ALRPH | 5 node | 66.6 | 68.0 | 7200 | 15.0 | 93.0 | 72.0 |

ALRPH = *Alternanthera philoxeroides* (Mart.) Griseb. (alligatorweed)
CYPES = *Cyperus esculentus* L. (yellow nutsedge)
ECHCG = *Echinochloa crus-galli* (L.) P. Beauv. (barnyardgrass)
ECHOR = *Echinochloa oryzoides* (Ard.) Fritsch (early watergrass)
ISCRU = *Ischaemum rugosum* Salisb. (saramollagrass)
LEFCH = *Leptochloa chinensis* (L.) Nees (Chinese sprangletop)
Compound II = benzyl 4-amino-3-chloro-5-fluoro-6-(4-chloro-2-fluoro-3-methoxyphenyl)pyridine-2-carboxylate.
ppb = parts per billion
lf = leaf The compositions and methods of the claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A composition for controlling aquatic weeds in a synergistically body of water, comprising a herbicidally effective amount of (a) a compound of formula (I) or a compound of formula (II),

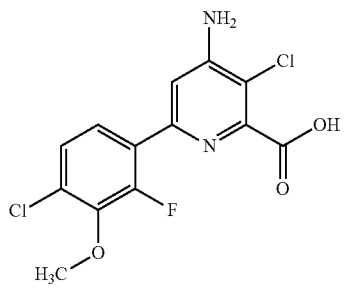

(I)

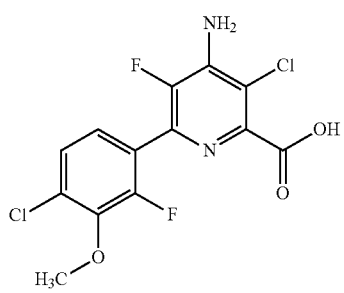

(II)

or an agriculturally acceptable salt or ester thereof, and (b) one or more of copper sulfate, mixed copper ethanolamine complex, diquat dibromide, endothal, or fluridone, or agriculturally acceptable salts or esters thereof.

2. The composition of claim 1, wherein (a) is halauxifen or an agriculturally acceptable salt or ester thereof.

3. The composition of claim 1, wherein (a) is halauxifen-methyl.

4. The composition of claim 1, wherein (a) is florpyrauxifen or an agriculturally acceptable ester or salt thereof.

5. The composition of claim 1, wherein (a) is florpyrauxifen-benzyl.

6. The composition of claim 1, wherein (b) is copper sulfate.

7. The composition of claim 6, wherein the weight ratio of (a) to copper sulfate is within the range of from about 1:27 to about 1:4.5.

8. The composition of claim 1, wherein (b) is mixed copper ethanolamine complex.

9. The composition of claim 8, wherein the weight ratio of (a) to mixed copper ethanolamine complex is within the range of from about 1:250 to about 1:15.

10. The composition of claim 1, wherein (b) is diquat dibromide.

11. The composition of claim 10, wherein the weight ratio of (a) to diquat dibromide is within the range of from about 1:220 to about 1:6.

12. The composition of claim 1, wherein (b) is endothal or an agriculturally acceptable salt or ester thereof.

13. The composition of claim 12, wherein the weight ratio of (a) to endothal or an agriculturally acceptable salt or ester thereof is within the range of from about 1:269 to about 1:8.

14. The composition of claim 1, wherein (b) is fluridone.

15. The composition of claim 14, wherein the weight ratio of (a) to fluridone is within the range of from about 1:6 to about 14:1.

16. A method for controlling aquatic weeds in a body of water, which comprises applying to the body of water the composition of claim 1.

17. The method of claim 16, wherein the aquatic weeds include hydrilla, curlyleaf pondweed, Eurasian watermilfoil, alligatorweed, yellow nutsedge, barnyardgrass, watergrass, *Echinochloa* species, saramollagrass or Chinese sprangletop.

18. The method of claim 16, wherein the final dilution level of (a) and (b) in the body of water is from about 0.25 parts-per-billion (ppb) to about 30,000 ppb.

19. The method of claim 16, wherein (b) is copper sulfate and the final dilution level of (a) and (b) in the body of water is from about 250 parts-per-billion (ppb) to about 2500 ppb.

20. The method of claim 16, wherein (b) is mixed copper ethanolamine complex and the final dilution level of (a) and (b) in the body of water is from about 200 parts-per-billion (ppb) to 10,000 ppb.

21. The method of claim 16, wherein (b) is diquat bromide and the final dilution level of (a) and (b) in the body of water is from about 700 parts-per-billion (ppb) to about 28,500 ppb.

22. The method of claim 16, wherein (b) is endothal or an agriculturally acceptable salt or ester thereof and the final dilution level of (a) and (b) in the body of water is from about 50 parts-per-billion (ppb) to about 10,500 ppb.

23. The method of claim 16, wherein (b) is fluridone and the final dilution level of (a) and (b) in the body of water is from about 5 parts-per-billion (ppb) to about 800 ppb.

24. The method of claim 16, wherein (a) and (b) are applied in conjunction with one or more other herbicides to control a wider variety of undesirable vegetation.

25. The method of claim 24, wherein the other herbicide includes one or more herbicides selected from the group consisting of flumioxazin, carfentrazone-ethyl, topramezone, aminopyralid, 2,4-D, 2,4-D choline salt, triclopyr, triclopyr choline salt, penoxsulam, imazamox, and bispyribac-sodium, and agriculturally acceptable salts or esters thereof.

26. The method of claim 16, wherein the aquatic weeds comprise a herbicide resistant or tolerant weed.

27. The method of claim 26, wherein the resistant or tolerant weed is a biotype with resistance or tolerance to single or multiple herbicides or single or multiple chemical classes, or inhibitors of single or multiple herbicide modes-of-action.

28. The method of claim 26 or 27, wherein the resistant or tolerant weed is a biotype resistant or tolerant to acetolactate synthase (ALS) or acetohydroxy acid synthase (AHAS) inhibitors, photosystem II inhibitors, acetyl CoA carboxylase (ACCase) inhibitors, photosystem I inhibitors, 5-enolpyruvyl-shikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, bleachers, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action, quinclorac, arylaminopropionic acids, difenzoquat or organoarsenicals.

\* \* \* \* \*